(12) United States Patent
Rössiger

(10) Patent No.: US 6,364,528 B1
(45) Date of Patent: Apr. 2, 2002

(54) DETERMINATION OF THE MEASURING SPOT DURING X-RAY FLUORESCENCE ANALYSIS

(75) Inventor: Volker Rössiger, Sindelfingen (DE)

(73) Assignee: Immobiliengesellschaft Helmut Fischer GmbH & Co. KG (DE)

( * ) Notice: Subject to any disclaimer, the term of this patent is extended or adjusted under 35 U.S.C. 154(b) by 0 days.

(21) Appl. No.: 09/374,331

(22) Filed: Aug. 13, 1999

(30) Foreign Application Priority Data

Aug. 14, 1998 (DE) .......................... 198 36 884

(51) Int. Cl.$^7$ .............................................. G01D 18/00
(52) U.S. Cl. .......................................... 378/207; 378/44
(58) Field of Search .............................. 378/44, 45, 207

(56) References Cited

U.S. PATENT DOCUMENTS 4,803,644 A    2/1989   Frazier et al.

OTHER PUBLICATIONS

Hasegawa Kiyoshi, May 19, 1995, Method for X–Ray Mapping Analysis, Patent Abstracts of Japan 07128259.

Mutsuo Sakamoto, Jul. 21, 1987, Method for Detecting Width of Composite Metal Stripe, Patent Abstract of Japan 6239706.

*Primary Examiner*—Craig E. Church
(74) *Attorney, Agent, or Firm*—McGlew and Tuttle, P.C.

(57) ABSTRACT

A specimen part for determining the intensity data of a measuring spot in X-ray fluorescent analysis is characterized in that it has a probe with a clearly defined contour surrounded by a surrounding material, the surrounding material and the probe material having the same linear attenuation coefficients for the emitted X-ray fluorescent radiation. With a method according to the invention it is possible to determine both the intensity centre and the contour of the measuring spot.

18 Claims, 3 Drawing Sheets

DETERMINATION OF THE MEASURING SPOT DURING X-RAY FLUORESCENCE ANALYSIS

FIELD OF THE INVENTION

The invention relates to a specimen part and to a method for the determination of the intensity data of a measuring spot in X-ray fluorescence analysis.

BACKGROUND OF THE INVENTION

If a substance is irradiated with hard, i.e. shortwave and therefore high energy X-radiation, electrons are ionized in the atoms of this substance, particularly the inner shells and as a consequence the vacancy is filled by electrons from the outer shells. The so-called X-ray fluorescent radiation (secondary radiation) is emitted and is softer, i.e. of a longer wave nature and therefore lower energy nature than the incident primary radiation. The emitted secondary radiation is characteristic for each atoms of the periodic system. Each X-ray fluorescent spectrum emitted by an atom comprises only a few characteristic lines, by means of which it is clearly identifiable. For quantitative analysis, apart from the wavelength, also the intensity, i.e. the amplitude of the emitted radiation is measured and this constitutes a measure of the content of the corresponding atomic species in the specimen, the coating thickness and the concentration of the corresponding atomic species.

X-ray fluorescence analysis is inter alia used as a method for non-destructive material testing for the analysis of coating thicknesses and compositions of coated and solid specimens, where it is of major importance, particularly when analyzing very small and/or structured specimens, such as conducting tracks, solder or bond faces, as well as other contact faces, such as electrolytic coatings.

In X-ray fluorescence analysis, the specimen to be investigated is excited to emit fluorescent radiation with the hard, polychromatic radiation of a X-ray tube. The primary beam incident on the specimen material is focussed either by means of collimators made from metal or glass or with focussing elements, such as glass capillaries. The analytical area of the specimen material excited by the primary beam or the surface of the primary radiation striking the specimen is known as the measuring spot. The size of the measuring spot of the X-ray fluorescence analysis of small test specimens is approximately 10 to 100 $\mu$m. The X-ray fluorescent radiation emitted by the specimen material is detected by means of suitable detectors, such as proportional counter tubes or semiconductor detectors.

Particularly when analyzing small specimens it is necessary not only to adequately define the geometrical dimensions of the measuring spot, but also to visibly represent the same in order to accurately position the specimen. For the representation of the measuring spot it is on the one hand necessary to determine the beam centre of the primary beam striking the specimen and on the other the spatial extension or the contour of the measuring spot.

For determining the beam centre it is e.g. known to displace over the width of the measuring spot the planar interface of a fluorescent material and also a non-fluorescent material in the case of an identical excitation and the emitted fluorescent radiation of the fluorescent material is measured for different relative positions with respect to the primary beam. If the interface is in the beam centre, the intensity of said fluorescent radiation is precisely half as large as if the entire surface of the fluorescent material was excited by the primary beam. This position with half the intensity is then used for the setting or adjustment of e.g. a cross-line or reticle of an observation instrument, such as a video camera.

A disadvantage of the described method is that, due to the mutually influencing, differing materials in the vicinity of their interfaces, it suffers from errors, particularly with small measuring spots. The reason for the errors is that the primary beam penetrates relatively deeply into the specimen and consequently fluorescent radiation not only occurs on the specimen surface, but also in deeper areas, so that the attenuation of the fluorescent radiation produced in the specimen material is important for the measured intensity. This follows the known attenuation law $$I = I_0 \cdot e^{-\mu x} \qquad (1)$$

in which $I_0$ is the intensity of the X-ray fluorescent radiation emitted directly at an excited atom and I is the radiation intensity after traversing the path x of a material with the linear attenuation coefficient $\mu$, which is dependent on the material.

For the determination of the geometrical dimensions (contour) of the measuring spot, it is known to estimate the same as a function of the cross-section of the collimator used or as a function of the distances between the radiation source, collimator and specimen. The shape and size of the actual measuring spot can diverge from the thus interpreted shape, because the fundamental assumptions only approximately correspond to reality, because the actual size and position of the projected spot of the radiation source are not precisely known. The primary beam axis also changes with respect to the optical axis due to thermal influences. Account is also not taken of the incomplete absorption of the primary radiation on the collimator edges. A divergence from the actual conditions (spot size, maladjustment of the beam centre) is not noticed.

It is also known for the determination of the measuring spot contour, to expose in place of a specimen a film material which is sensitive to X-radiation and whose wavelength is in the primary radiation range. Although this method provides a realistic image of the measuring spot, the film material must be removed for development and the beam centre information is lost.

Whilst avoiding the aforementioned disadvantages, the problem of the invention is to propose a specimen part and a method for determining both the intensity centre and also the intensity distribution of a measuring spot, i.e. the intensity data of an X-ray striking a surface in the case of X-ray fluorescence analysis.

SUMMARY OF THE INVENTION

According to the invention, the problem is solved with a specimen part for the determination of intensity data of a measuring spot in X-ray fluorescence analysis, in that the specimen part has a probe with a clearly defined contour surrounded by a surrounding material, said surrounding material and the probe material having the same linear attenuation coefficients for the emitted X-ray fluorescent radiation.

For the determination of the intensity centre of the measuring spot, the specimen part according to the invention is moved over the width of the measuring spot, so that either the probe or surrounding material or both the probe and the surrounding material are excited with primary radiation. As the probe and surrounding material differ, the characteristic fluorescence spectra can differ. Since, according to the invention, the probe material and the surrounding material have the same linear attenuation coefficients for the emitted fluorescent radiation, the intensities (amplitudes) of the fluorescent radiation emitted in different depths of the probe and the surrounding material of the specimen part are attenuated or absorbed in the same way, so that at the boundary between the probe and the surrounding material there is no mutual influencing of the segments and the intensities of the fluorescence spectra emitted by the probe and surrounding material are comparable. A secondary beam e.g. emitted in a lower plane of the probe, consequently undergoes the same attenuation in the surrounding material after passing out of the probe material.

The specimen part according to the invention can e.g. be firmly connected to a programmable specimen table, with which it is possible to perform clearly defined positional displacements relative to the fixed primary beam.

The specimen part comprising the probe and the surrounding material preferably has a planar surface, so that the probe is aligned with the surronding material and no absorption and scattering effects take place on projecting edges.

According to a preferred embodiment, the probe and the surrounding material are saturation-tight in the X-ray fluorescence sense. The clearly defined shape of the probe of the inventive specimen part can e.g. be circular or polygonal. The cross-sectional dimensions of the probe are preferably smaller than the cross-section of the incident primary beam on the specimen part and preferably smaller than 100 μm. If the probe surface is smaller than the measuring spot, the intensity distribution of the primary beam determined via the intensity of the emitted fluorescent radiation already represents a realistic model of the intensity profile of the primary beam, in that the intensity maximum is recognized as a discreet peak. If the probe surface is larger than the measuring spot, then the intensity maximum is detected as a plateau. The probe can e.g. comprise a piece of wire embedded in the surrounding material.

As has already been stated, the probe and the surrounding material comprise different materials with consequently differing fluorescence spectra, but with identical linear attenuation coefficients for the emitted fluorescent radiation. For example, both components, i.e. the probe and the surrounding material can comprise alloys having different alloy constituents, or either the probe or the surrounding material can be formed from a pure metal, whereas the in each case other component comprises an alloy, which does not contain as an alloy constituent said pure metal. The choice of a metal for the probe and an alloy with the same linear attenuation coefficients is explained hereinafter.

The problem is solved by a method for determining the intensity data of a measuring spot during X-ray fluorescence analysis in that the X-ray fluorescent radiation is measured at least for several relative positions of the measuring spot and a specimen part comprising a probe with a clearly defined contour and a surrounding material with the same linear attenuation coefficients.

The materials of the probe and the surrounding material are chosen in such a way that they have an identical, linear attenuation coefficient and at least one of the materials, on excitation with X-ray quanta, whose wavelength is in the wavelength range of the primary beam, emits fluorescent radiation. For determining the intensity centre of the measuring spot or the primary beam striking the specimen part, it is possible to measure either the fluorescent radiation of the probe or the surrounding material for several relative positions of probe and measuring spot. Whereas in the first case the intensity centre of the measured X-ray fluorescent radiation corresponds to the intensity centre of the measuring spot, in the second case the measured intensity minimum of the X-ray fluorescent radiation corresponds to the intensity centre of the measuring spot, the intensity centre of the measuring spot or measuring spot centre in each case being obtained for the particular specimen part position in which the probe, which is preferably small compared with the measuring spot, is congruent with the intensity maximum of said spot. If the materials of the probe and the surrounding material are chosen in such a way that only one of the materials emits fluorescent radiation on excitation with X-ray quanta in the wavelength range of the primary beam, overlaps of lines of the fluorescence spectra of probe and surrounding material are excluded.

For marking the thus emitted measuring spot centre, it is possible to use as the adjusting means in known manner a reticle of an observation instrument, e.g. a video camera, so that the reticle is superimposed on the measuring spot centre. In a preferred variant, the specimen part is installed firmly on a preferably programmable specimen table, so that the probe is displaced by means of programmable pivoting movements of the specimen table relative to the fixed primary beam.

For the determination of the intensity distribution or the contour of the measuring spot, according to a preferred variant a numerical approximation is provided, which is performed after determining the measuring spot centre. The numerical approximation is based on the fact that the intensity of the emitted X-ray fluorescent radiation measured by means of the inventive specimen part is proportional to that fraction of the primary beam which covers the probe surface. The measured intensity I (x, y) of the emitted X-ray fluorescent radiation as a function of the space coordinates x and y, which stretch over a planar coordinate system parallel to the planar surface of the inventive specimen part, can be described by the following equation (2):

$$I(x, y) = K \cdot \int p(x', y') dx' dy' \quad (2)$$

in which p (x', y') is the lateral intensity distribution of the primary radiation and K is a material constant, which takes account of the intensity ratio between primary and secondary radiation (emitted X-ray fluorescent radiation) e.g. of the probe material and the integral of the lateral intensity distribution p (x, y) is to be formed over the probe surface S=f (x, y), in which the space coordinates x and y preferably mark the centre of the probe surfaces. The above equation (2) describes the relationship of the intensities of the measured secondary radiation I and primary radiation p for the case that the X-ray fluorescent radiation of the probe is measured and consequently with a full-surface irradiation of the probe with the primary beam an intensity centre of the fluorescent radiation is obtained. However, if the X-ray fluorescent radiation of the surrounding material is measured and consequently an intensity minimum of the fluorescent radiation is obtained for a full-surface irradiation of the probe, then on the left-hand side of equation (2) $I_{max}$ is to be introduced in place of I (x, y), in which $I_{max}$ is the maximum fluorescent radiation intensity well outside the probe in the case of a full-surface irradiation of the surrounding material.

For the determination of the lateral intensity distribution p (x', y') of the primary beam, preferably a two-step staircase function is chosen as the mathematical statement and the values thereon vary between 0 (well outside the measuring spot) and $p_{max}$ (in the centre of the measuring spot). For this purpose the measuring spot is subdivided in grid-like manner into N surface elements of clearly defined size and contour for which the intensity p (x', y') is assumed to be constant. This approximation has proved to be adequately precise, particularly for very small surface elements.

Assuming that the intensity p of the primary beam is constant for each surface element dx·d, it is possible to implement equation (3):

$$I(x, y) = K \cdot \Sigma a_{ij(x,y)} \cdot p_{ij} \quad (3)$$

in which K is a constant.

If e.g. the fluorescent radiation I of the probe is measured, then the coefficients $a_{ij}$ describe the covering of the ij-th surface element with the probe surface. If the ij-th surface element is entirely on the surrounding material. then a has the value 0. It the ij-th surface element is completely on the probe, then a=1. The intensities $P_i$ of the primary beam to be determined for different relative positions of the primary beam and the specimen part according to the invention are preferably determined by means of a linear equation system, in which for each position of the specimen part in the grid of N surface elements the fluorescent radiation I is determined and consequently N equations are obtained.

In order to statistically secure the measured values I of the fluorescent radiation obtained for the determination of the contour of the measuring spot or in order to be able to estimate their variance and standard deviation, preferably for each surface element in the raster there is a multiple determination of the established intensity I of the X-ray fluorescent radiation and in each case the mean values of the multiple determinations are used in equation (3).

The measuring spot contour obtained in the described manner can e.g. be checked with an observation instrument, such as a video camera, in that the calculated measuring spot contour and the measuring spot centre is faded into the observation instrument monitor.

The four different materials of the specimen part are joined together orthogonally in section-like manner. The beam centre is identical to the visible intersection of the sectors, if the relative fluorescence intensities of all four materials are in each case 25%. In a highly preferred development, a preliminary centering can take place. In this case four materials abutting at a common contact point and having known fluorescence spectra are provided and in particular the probe is embedded in one of the four materials as the surrounding material. An adjustment takes place in such a way that the probe or surrounding material is used without secondary excitation and that the fluorescent radiation of the material having no secondary excitation is measured. Moreover, by measuring the fluorescence spectrum by means of an adjusting part with four materials abutting at a common contact edge, the impact point is determined as a primary beam relative to the common contact edge and in particular the impact point of the primary beam is made to coincide with the contact edge and generally the specimen part is moved. Such a procedure is advantageous with very small beam diameters of 20 μm or less and correspondingly small specimen parts of 50 μm or less, because then the number of quantities for the intensity centre determination can be reduced.

BRIEF DESCRIPTION OF THE DRAWINGS

The invention is described in greater detail hereinafter relative to a preferred embodiment and with reference to the attached drawings, wherein show.

DETAILED DESCRIPTION OF THE DRAWINGS

Figure 1:
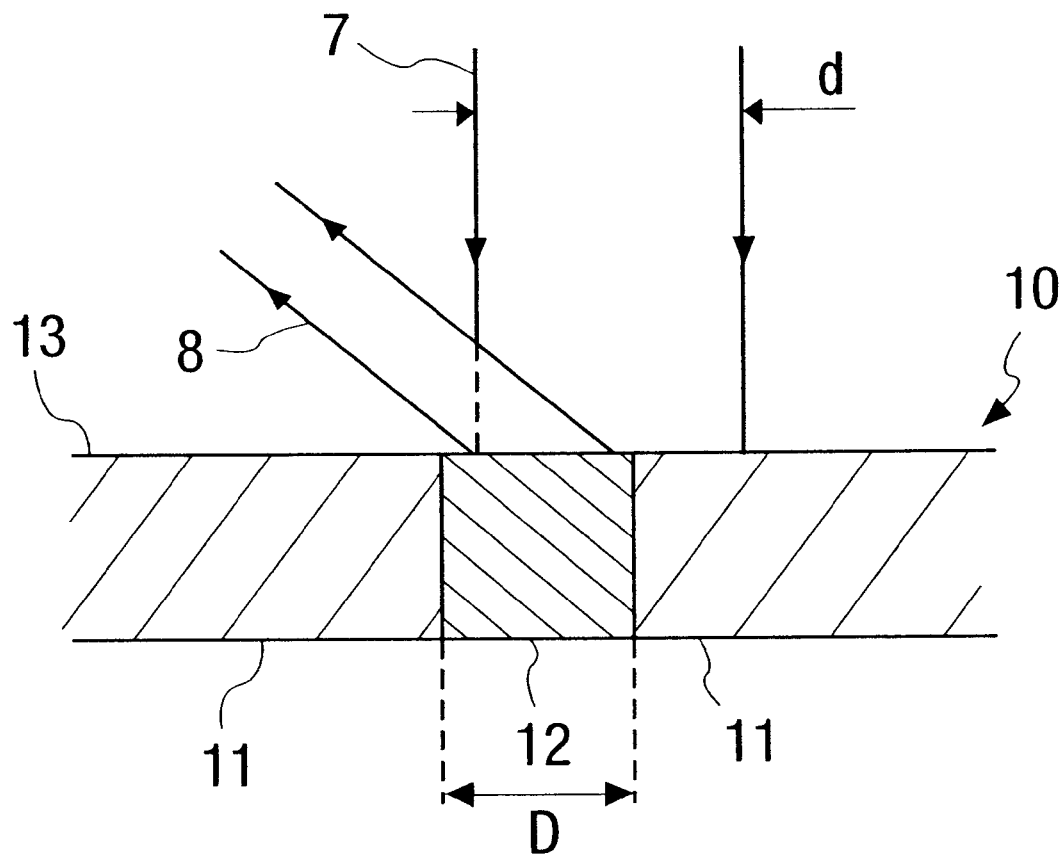
FIG. 1 A cross-section through a specimen part according to the invention.

An X-ray fluorescent analysis arrangement has a X-ray tube as the radiation source and emits as primary radiation 7 shortwave and therefore high energy X-ray quanta. The primary beam 7 is focussed with a collimator, so that the specimen part 10 is excited with substantially parallel-incident primary beam 7. By exciting the specimen part 10 with high energy X-ray quanta 7, it emits X-ray fluorescent radiation 8 (secondary radiation), which can be directed parallel with a further collimator and is received by a receiver 6.

The specimen part 10 according to the invention shown in cross-section in FIG. 1 comprises a probe 12 and surrounding material 11 and has a planar surface 13. The transverse dimensions D of the probe 12 are smaller than the transverse dimensions d of the incident primary beam 7 or the measuring spot (FIG. 2), so that the intensity centre of the primary beam 8 is detectable as a peak. The materials 11, 12 are e.g. chosen in such a way that in the wavelength range of the excitation only the probe material 12 emits fluorescent radiation 8.

Figure 2:
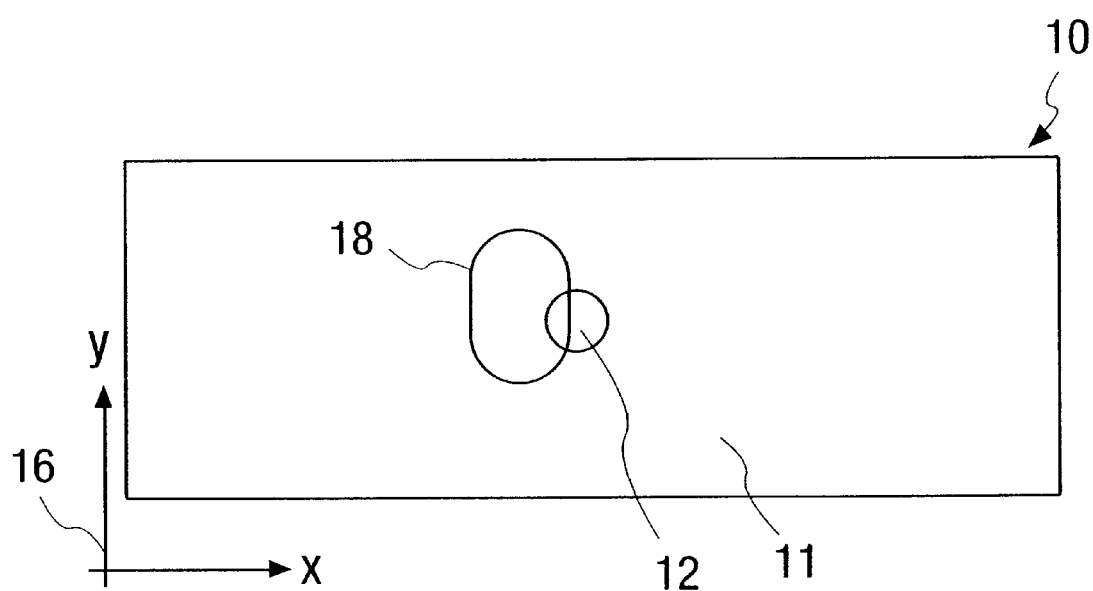
FIG. 2 A plan view of a specimen part according to the invention.

FIG. 2 shows in plan view the inventive specimen part 10. The specimen part 10 is e.g. firmly installed on a programmable, not shown specimen table, by means of which the probe 12 is movable relative to the fixed measuring spot 18 in the x and y-directions of the coordinate system 16.

Figure 3:
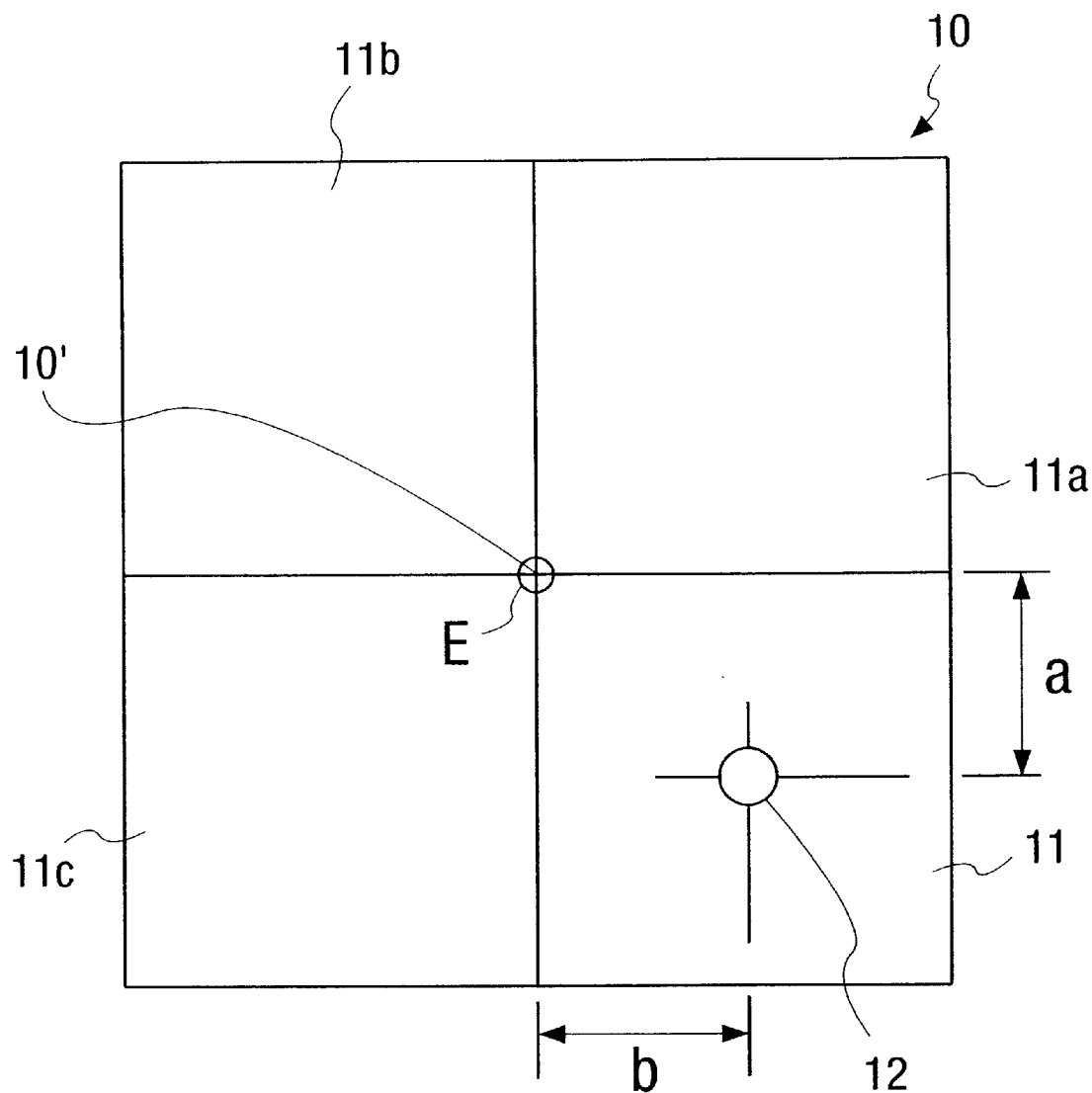
FIG. 3 A specimen part with four quadrants and a probe embedded in one quadrant.

FIG. 3 shows a specimen part 10 with four quadrants 11, 11a, 11b, 11c, which meet in a common edge 10' (parallel to the incidence direction E of the X-ray), and consequently form in the surface of the specimen part 10 an intersection. In one of the quadrants is formed the surrounding material 11 for the probe 12. The specimen part 10 is firmly connected to a programmable measuring spot. The spectra of the four materials of the four quadrants 11, 11a, 11b, 11c are known. By means of an actually measured spectrum the position of the measuring spot relative to the contact edge 10' or the intersection formed by it in the surface is obtained. The specimen part 10 can be moved under the X-ray in such a way that the beams reach the intersection. In this case the beam centre is substantially identical with the intersection, if the relative fluorescence intensities of all four materials are in each case 25% On the basis of the known protoconal spacings a and b of probe 12 from edge 10', the X-ray can be brought into the vicinity of the probe 12 and then the inventive method can be performed for the precise determination of the intensity data of the primary beam or measuring spot. In a specific embodiment, a thin nickel wire is embedded in an AlSn alloy as the surrounding material and embedding can take place by pressing in. There is a planar grinding or finishing transversely to the wire direction, which leads to a planar surface of the entire specimen part 10, i.e. probe 12 and surrounding material 11.

As stated, the linear attenuation coefficient of the measured X-ray fluorescent radiation component of the surrounding material 11 should correspond to the linear attenuation component of the probe material. As a good approximation for alloys the linear attenuation coefficients behave as a weighted mean corresponding to the mass fractions. The linear attenuation coefficient $\mu_{AlSn}$ of an AlSn alloy with the Sn mass fraction $C_{Sn}$ is then $$\mu_{AlSn}(C_{Sn}) = C_{Sn} \cdot \mu_{Sn} + (1 - C_{Sn}) \cdot \mu_{Al}$$

The linear attenuation coefficient $\mu_{AlSn}$ of the AlSn alloy is to be the same as the linear attenuation coefficient of the probe material Ni and namely for the energy of the Ni-K-α-component. The attenuation coefficients of the three materials used are: $\mu_{Ni}$=535 cm−1, $\mu_{Sn}$=2150 cm$^{-1}$ and $\mu_{Al}$=145 cm$^{-1}$. Thus, using the above equation, there is a mass fraction of 20% Sn for an alloy, whose linear attenuation coefficient corresponds to that of the probe material nickel. With such a specimen part the intensity data were determined in accordance with the invention and repeated tests gave a reproducibility of the intensity centre with a precision of 1 μm.

What is claimed is:

1. A method for determining intensity of a measuring spot in X-ray fluorescence analysis, the method comprising the steps of:

providing a calibration tool with a first material surrounded by second material, said first and said second material defining a contour, said first and said second material have a similar linear attenuation coefficient;

irradiating said calibration tool with X-radiation formed into the measuring spot to cause said calibration tool to emit X-ray fluorescent radiation;

measuring an intensity of the X-ray fluorescent radiation from said calibration tool for a plurality of relative positions of the measuring spot with respect to said first material;

determining a position of the measuring spot relative to said calibration tool from said measured intensity of the X-ray fluorescent radiation from said calibration tool.

2. A method according to claim 1, wherein:
X-ray fluorescent radiation of said probe is measured.

3. A method according to claim 2, further comprising:
determining a center of an intensity distribution of the emitted X-ray fluorescent radiation;

associating said center of said intensity distribution of the emitted X-ray fluorescent radiation with a position of said probe as a measuring spot center.

4. A method according to claim 1, wherein:
X-ray fluorescent radiation of said surrounding material is measured.

5. A method according to claim 4, further comprising:
determining an intensity distribution of the emitted X-ray fluorescent radiation;

inverting said intensity distribution by a linear transformation to have a maximum value equal one and have a minimum value equal zero;

associating a center of said inverted intensity distribution with a position of the probe as a measuring spot center.

6. A method according to claim 1, wherein:
said measuring spot center is marked by superimposing with an adjusting means.

7. A method according to claim 6, wherein:
said adjusting means includes a reticle of an observation instrument.

8. A method according to claim 1, wherein:
said specimen is firmly installed on a programmable specimen table to move said probe relative to the measuring spot center.

9. A method according to claim 1, wherein:
said determinating of the intensity distribution of said measuring spot in X-ray fluorescence analysis for determining the measuring spot center is carried out by numerical approximation.

10. A method according to claim 9, wherein:
the intensity $p_i$ of a primary beam in the intensity distribution is described by I(x, y) and is approximated by a portion-wise constant function $$P(x,y)=P_{ij} \text{ for } x_i<=<x_{i+1}$$

and for $y_j<=y<y_{j+1}$ in which an intensity of primary radiation and the coordinates x and y are identical with the center of the probe.

11. A method according to claim 9, wherein:
the intensities I(x, y) of the emitted X-ray fluorescent radiation, measured in a x-y grid, which at least partly covers the measuring spot, are described by the equation $$I(x, y)=K^*\Sigma a_{ij}(x, y)^*p_{ij}$$

in which K is a constant and $a_{ij}(x,y)$ are coefficients for describing the coverage of the surface element ij ($x_i<= x<x_{i+1}$, and for $y_i<=y<y_{j+1}$) and the probe surface at position (x, y); and $p_{ij}$ is a constant assumed intensity of the primary beam in said surface element ij and in which the summation takes place over all the surface elements ij.

12. A method according to claim 9, wherein:
said determining of the intensity p of the primary radiation includes determining the emitted X-ray fluorescent radiation several times in each surface element.

13. A method according to claim 12, wherein:
mean values from said determining several times are used for the intensities I(i).

14. A method according to claim 1 wherein:
said probe or said surrounding material without secondary excitation is used and that an absence of fluorescent radiation from the material having no secondary excitation is detected.

15. A method according to claim 1, further comprising:
providing an X-ray tube;
emitting X-ray radiation from the X-ray tube as a measuring spot toward the specimen;
moving the measuring spot across the probe and the surrounding maternal in the specimen.

16. A method according to claim 1, further comprising:
measuring a fluorescent spectrum by means of an adjustment part with four materials abutting at a common contact edge, an impact point is determined as a primary beam relative to the common contact edge.

17. A method according to claim 16, wherein:
the impact point of the primary beam is made to coincide with the contact edge.

18. A method according to claim 17, wherein:
the impact point of the primary beam is brought to the probe and then the intensity data of the measuring field are determined on a basis of known relative coordinates of the probe with respect to the contact edge.

* * * * *